United States Patent [19]

Zavareh et al.

[11] Patent Number: 5,777,124
[45] Date of Patent: Jul. 7, 1998

[54] PROCESS FOR PREPARING LEVOBUPIVACAINE AND ANALOGUES THEREOF

[75] Inventors: Hooshang Shahriari Zavareh; Graham Anthony Charles Frampton, both of Cambridge, United Kingdom

[73] Assignee: Chiroscience Limited, Cambridge, United Kingdom

[21] Appl. No.: 836,449

[22] PCT Filed: Oct. 23, 1995

[86] PCT No.: PCT/GB95/02514

§ 371 Date: Apr. 25, 1997

§ 102(e) Date: Apr. 25, 1997

[87] PCT Pub. No.: WO96/12700

PCT Pub. Date: May 2, 1996

[30] Foreign Application Priority Data

Oct. 25, 1994 [GB] United Kingdom ............... 9421478
Mar. 10, 1995 [GB] United Kingdom ............... 9504925

[51] Int. Cl.$^6$ .................................................. C07D 211/60
[52] U.S. Cl. ..................................................... 546/225
[58] Field of Search ............................ 546/225; 540/224

[56] References Cited

U.S. PATENT DOCUMENTS 4,695,576  9/1987  af Ekenstam et al. ............ 514/330

FOREIGN PATENT DOCUMENTS 1166802  10/1969  United Kingdom.
WO85/00599  2/1985  WIPO.

OTHER PUBLICATIONS

Vecchietti et al. J. Med. Chem., vol. 34, No. 1, pp. 397–403, 1991.

Pizey et al. Synthetic Reagents, vol. I, Chapter 4, pp. 333–336, 1974.

March, J., Advanced Organic Chemistry, third edition, p. 388.

*Primary Examiner*—Zinna Northington Davis
*Attorney, Agent, or Firm*—Saliwanchik, Lloyd & Saliwanchik

[57] ABSTRACT

A process for preparing levobupivacaine, racemic bupivacaine or another N-alkyl analogue thereof, comprises chlorinating pipecolic acid hydrochloride, amidation of the resultant pipecolyl chloride hydrochloride in solvent, without isolation, with 2,6-dimethylaniline, and alkylation of the resultant pipecolic acid 2,6-xylidide. Alternatively, the alkylation may be followed by the amidation.

12 Claims, No Drawings

PROCESS FOR PREPARING LEVOBUPIVACAINE AND ANALOGUES THEREOF

CROSS-REFERENCE TO RELATED APPLICATION

This application is a 371 of International Application No. PCT/GB95/02514 filed Oct. 23, 1995.

FIELD OF THE INVENTION

This invention relates to a novel process for the manufacture of racemic bupivacaine or levobupivacaine, and analogues thereof, from pipecolic acid.

BACKGROUND TO THE INVENTION

Bupivacaine (formula I in Scheme 1) and ropivacaine are well-known local anaesthetics. They are described in U.S. Pat. No. 4,695,576, GB-A-1166802, and PCT/NO83/00029. The corresponding N-methyl and N-cyclopropyl compounds also have such activity. However, the production of such material on a large scale, from pipecolic acid, suffers from various difficulties.

Phosphorus pentachloride has been used as a chlorinating agent. On a large scale, its use is problematic, in that. $PCl_5$ is liable to react with atmospheric moisture, and to generate waste whose separation from the acid chloride intermediate (II) is difficult. Furthermore, the phosphate waste streams which are generated are difficult to treat or otherwise discard.

The use of acetyl chloride as the process solvent for the production of the acid chloride (II) poses similar difficulties.

Whereas isolation of the intermediate acid chloride (II) as described in the art can be carried out on a laboratory scale, its isolation on the larger scale is impractical. This is due to the fact that the intermediate (II) is a very labile substance and may decompose upon exposure to atmospheric moisture.

Washing of the isolated acid chloride (II) with commercial grade acetone, as described in the art, will lead to its decomposition, as commercial acetone usually contains some water.

Reaction of the acid chloride (II) with 2,6-dimethylaniline in a mixture of acetone and N-methylpyrrolidone (NMP), as advocated in the art, leads to the formation of pipecolic acid 2,6-xylidide (III) which is difficult to isolate from the reaction medium.

Alkylation of the intermediate (III) with 1-bromobutane and potassium carbonate in n-butanol affords comparatively poor yield of the desired bupivacaine, since the reaction proceeds very slowly and usually does not go to completion.

SUMMARY OF THE INVENTION

The present invention describes a practical and streamlined one-pot process which is both economical and viable for scale-up. Furthermore, this invention may be used to manufacture racemic bupivacaine, levobupivacaine, or any corresponding N-alkylated material such as ropivacaine (Pr rather than Bu) in racemic or enantiomeric form.

According to this invention, pipecolic acid is initially reacted with hydrogen chloride in a suitable solvent, furnishing pipecolic acid hydrochloride salt.

This compound is not isolated from the reaction medium but is directly treated with thionyl chloride, whereupon pipecolic acid chloride hydrochloride (II) is produced. Other chlorinating agents may be used, provided that they do not contain phosphorus, e.g. oxalyl chloride.

Again, this intermediate is not isolated and is conveniently treated with (2 equivalents of) 2,6-dimethylaniline. This operation generates the HCl salt of the intermediate (III) which is later isolated, after work-up. By controlling the pH, the free base can be obtained, essentially uncontaminated with 2,6-dimethylaniline (which is released as the pH is increased).

Alkylation of the free base of intermediate (III) is carried out with an alkylating agent such as 1-bromobutane in a suitable solvent such as acetonitrile (ACN) or advantageously in dimethylformamide (DMF) in the presence of a suitable base such as potassium carbonate. The reaction proceeds rapidly, and the resulting free base of, say, bupivacaine is isolated after removal of the solvent.

The free base may then be dissolved in a suitable solvent such as isopropanol and treated with hydrogen chloride, affording the HCl salt of, say, bupivacaine which is recovered by filtration (see Scheme 1).

It appears that no significant racemisation occurs during this novel process. Therefore, for example, by using enantiomerically pure (S)-pipecolic acid in this process, levobupivacaine can be produced.

DESCRIPTION OF THE INVENTION

The process of the invention is carried out by the steps described above. If desired, alkylation may precede amidation. An alternative preparation of the free base (III) is described in our International Patent Application No. PCT/GB95/02385.

The following Examples illustrate the invention.

Example 1 Pipecolic Acid 2,6-Xylidide

Pipecolic acid (130 g) was suspended in 2 l toluene and was stirred at ambient temperature. Hydrogen chloride (40 g) was added slowly during 30 minutes.

The mixture was heated to 55° C. and 1 g of DMF was added, followed by the addition of thionyl chloride (120 g) during 1.5 hours. The stirring at this temperature was continued until evolution of gases ceased.

2,6-Dimethylaniline (242 g) in toluene (250 ml) was added to the mixture at such a rate that the temperature of the mixture was maintained below 60° C. After 2 hours, the mixture was filtered and washed with toluene (200 ml). The resulting solid was dissolved in water (2.5 l) and was treated with aqueous NaOH until its pH was raised to 4.5–5.5. The liberated 2,6-dimethylaniline was removed by extraction with toluene.

The pH of the aqueous layer was raised still further, to 11–12, whereupon pipecolic acid-2,6-xylidide (III) was liberated. This intermediate was extracted with toluene and was obtained after removal of the solvent as a crystalline solid (151 g, 65% of theory).

Example 2 N-n-Butylpipecolic Acid 2,6-Xylidide

1-Bromobutane (90 g) was added to a suspension of pipecolic acid-2,6-xylidide (140 g) and a potassium carbonate (100 g) in DMF (330 ml). The mixture was stirred and heated at 80° C. for 90 minutes and then was allowed to cool to 35° C. The solids were filtered off and the DMF solution was added to cold water (1.5 l) whereupon N-n butylpipecolic acid 2,6-xylidide precipitated as a pale cream solid (159 g, 92% theory).

Example 3 N-n-Butylpipecolic Acid 2,6-Xylidide HCl Salt

Hydrogen chloride (25 g) was introduced slowly into a stirred solution of N-n-butylpipecolic acid 2,6-xylidide (145 g) in isopropanol (250 ml) at ambient temperature. The resulting white product was filtered off, washed with isopropanol and dried under vacuum to constant weight (161 g, 99% theory).

In order to prepare levobupivacaine, by the process of the present invention, a first route involves preparing and then resolving racemic bupivacaine. A racemisation process is described in International Patent Application No. PCT/GB95/02247. A second route involves starting from the appropriate pipecolate enantiomer.

Scheme 1: A Novel Method for the Manufacture of Bupivacaine

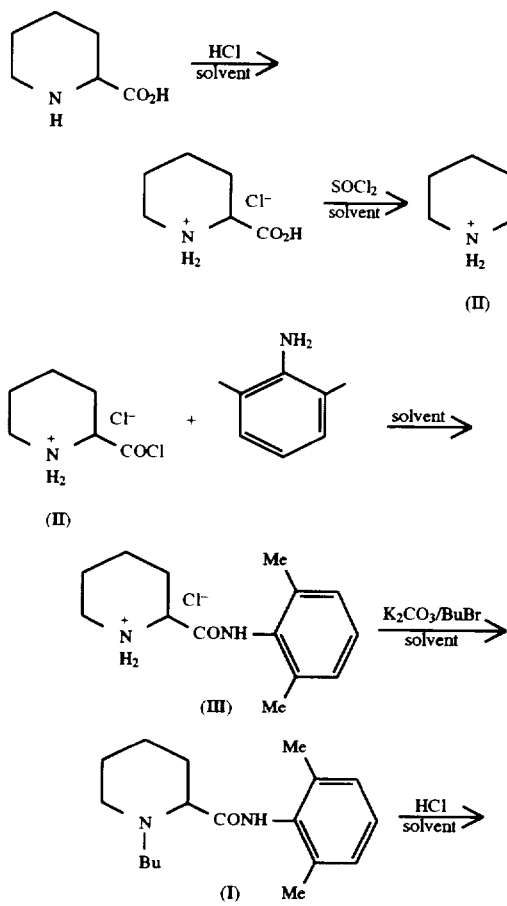

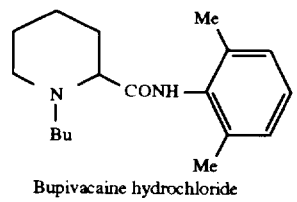

Bupivacaine hydrochloride

We claim:
1. A process for preparing a 1-alkyl-N-(2,6-dimethylphenyl)-2-piperidinecarboxamide, as the free base or a salt thereof, which comprises the steps of:
   (i) reacting pipecolic acid hydrochloride with an excess of a P-free chlorinating agent in a solvent, and distilling off said chlorinating agent;
   (ii) reacting the resultant pipecolyl chloride hydrochloride in solvent, without isolation, with excess 2,6-dimethylaniline;
   (iii) raising the pH to separate the resultant pipecolic acid 2,6-xylidide from excess 2,6-dimethylaniline;
   (iv) alkylating said 2,6-xylidide; and,
   (v) isolating the product from the reaction mixture.
2. The process, according to claim 1, wherein the solvent in steps (i) and (ii) is selected from the group consisting of a hydrocarbon, halogenated hydrocarbon and ether.
3. The process, according to claim 2, wherein the solvent is selected from the group consisting of toluene, methyl tert-butyl ether and tetrahydrofuran.
4. The process, according to claim 1, wherein the alkylation is conducted in a solvent that solvates $K_2CO_3$ and is water-miscible.
5. The process, according to claim 4, wherein said water-miscible solvent is DMF or acetonitrile.
6. The process, according to claim 1, whereby (S)-pipecolic acid is converted to levobupivacaine.
7. The process, according to claim 1, wherein the product is racemic bupivacaine.
8. The process, according to claim 1, wherein the product is 1-propyl-N-(2,6-dimethylphenyl)-2-piperidinecarboxamide, in racemic or optically-enriched form.
9. The process, according to claim 1, wherein the amidation comprises using 2 equivalents of 2,6-dimethylaniline.
10. The process, according to claim 1, wherein said chlorinating agent is $SOCl_2$ or oxalyl chloride.
11. The process, according to claim 1, wherein said chlorinating agent is distilled off with HCl.
12. The process, according to claim 1, wherein step (iv) is followed by conversion of the resultant free base product to a salt thereof and then proceeding to step (v).

* * * * *